United States Patent [19]

Bass et al.

[11] 4,008,325

[45] Feb. 15, 1977

[54] CONTROL OF RICE BLAST DISEASE EMPLOYING CERTAIN PYRIDO COMPOUNDS

[75] Inventors: Robert J. Bass, Birchington, England; Richard C. Koch, Niantic, Conn.; Hugh C. Richards; John E. Thorpe, both of Canterbury, England

[73] Assignee: Pfizer Inc., New York, N.Y.

[22] Filed: July 25, 1975

[21] Appl. No.: 598,747

Related U.S. Application Data

[62] Division of Ser. No. 361,200, May 17, 1973, Pat. No. 3,917,838.

[30] Foreign Application Priority Data

May 17, 1972 United Kingdom ............ 23158/72

[52] U.S. Cl. .................................. 424/258
[51] Int. Cl.² .............................. A01N 9/22
[58] Field of Search .................... 424/258

[56] References Cited

UNITED STATES PATENTS 3,917,838  11/1975  Bass et al. ................. 424/258
3,924,042  12/1975  Gerster ....................... 424/258

*Primary Examiner*—V. D. Turner
*Attorney, Agent, or Firm*—Connolly and Hutz

[57] ABSTRACT

A method of treatment or control of diseases of rice plants comprising contacting the plants, and the seeds thereof with an effective amount of a compound of the formula:

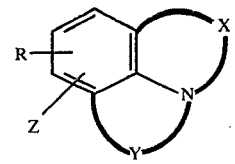

or a non-phytotoxic acid addition salt thereof, wherein each of X and Y completes a saturated or unsaturated pyrrolo- or pyrido-ring;

X and Y may each be substituted with up to two substituents selected from halo, lower alkyl, phenyl, oxo or thio;

and R is hydrogen, lower akyl, lower alkoxy, lower alkanoyl, benzoyl, hydroxy, lower alkanoyloxy, cyano, or halo; and Z is hydrogen or halo.

Certain of these compounds are novel compounds and are claimed as such. Compositions for the treatment of plant diseases are also claimed.

3 Claims, No Drawings

CONTROL OF RICE BLAST DISEASE EMPLOYING CERTAIN PYRIDO COMPOUNDS

CROSS REFERENCE TO RELATED APPLICATION

This application is a divisional of application Ser. No. 361,200 filed May 17, 1973, and now U.S. Pat. No. 3,917,838.

BACKGROUND OF THE INVENTION

This invention relates to the treatment or control of plant diseases and is particularly concerned with the treatment or control of fungal and bacterial diseases of the rice plant. It is also concerned with novel compositions for the treatment or control of plant diseases and with novel compounds for use in such compositions.

Rice, one of the most important cereal grains, is grown in coastal plains, tidal deltas, and river basins in temperate, tropical and semi-tropical regions. It is the staple food of a large segment of the world's population, the major part of which depends almost entirely upon rice and lives in the poorer and more thickly populated areas of the rice-growing regions.

Rice, or more correctly, the rice plant, like all field crops, is subject to a variety of diseases, the most serious of which is rice blast, a fungal disease caused by *Piricularia oryzae*. The disease is prevalent in most of the humid rice-producing regions of the world. The aerial part of the plant is attacked. The most conspicuous symptom is neck rot which is characterized by the necks breaking over. Other symptoms are the blighting or blasting of the heads, spots on the leaves, leaft sheaths and stems. The overall result of the disease is a decrease in yield and quality of the rice. The rice plant is likewise subject to fungal disease (sheath blight) caused by *Corticium sasakii* as well as bacterial attack (leaft blight) caused by *Xanthomonas oryzae*.

Control measures appear to have developed along two principal lines, cultural and chemical. The various cultural control measures developed include production of resistant varieties of rice, timing of transplanting, clean cultivation, seed selection and controlled irrigation.

Chemical measures of control such as the use of fungicidal seed dressings and foliage fungicides are prophylactic in nature and have little if any therapeutic value. The agents most commonly used for such treatments are organic mercurials, copper sulfate, benzoquinones, naphthoquinones, thiuram disulfate, dithiocarbamates, pentachlorobenzyl alcohol and O,O-diethyl-S-benzylthiophosphate. More recently, therapeutic measures of control using antibiotics such as blasticidin, kasugamycin and blasticidin-S-benzylamino-benzene sulfonate have come into use.

Such chemical methods of control, however, are not satisfactory for one or more reasons such as a low level of effectiveness, inhibition of seed germination, tendency toward phytotoxic effects, high material costs, and in the case of mercury compounds, the presence of toxic residue on the treated crop. Additionally, the use of blasticidin requires extreme care in its use because of its toxicity.

SUMMARY OF THE INVENTION

According to the present invention, a method for the treatment or control of fungal and/or bacterial diseases of plants, especially the rice plant, comprises contacting the plant, or the seeds thereof, with a fungicidally and/or bactericidally effective amount of a pyrroloindole, pyrrolo-quinoline or pyrido-quinoline compound of the formula:

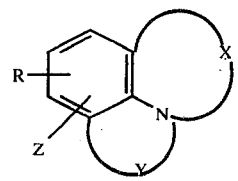

wherein
each of X and Y completes a saturated or unsaturated pyrrolo- or pyrido- ring;
X and Y may each be substituted with one or more halogen atoms or lower alkyl or phenyl groups;
X and/or Y may be substituted with one or more oxo or thio groups;
R represents hydrogen or a lower alkyl, lower alkoxy, lower alkanoyl, benzoyl, hydroxy, lower alkanoyloxy or cyano group or a halogen atom; and Z is hydrogen or halo; or a non-phytotoxic acid addition salt thereof.

Preferred are the instances in which:
each of X and Y completes a saturated or unsaturated pyrrolo- or pyrido ring:
X and Y may each be substituted with up to two substituents selected from halo, lower alkyl, phenyl, oxo, or thio;
R is hydrogen, lower alkyl, lower alkoxy, lower alkanoyl, benzoyl, hydroxy, lower alkanoyloxy, cyano or halo; and
Z is hydrogen or halo.

In the formula I, when X and Y are each unsubstituted, they may be any of the groups (a): $-CH_2CH_2-$, $-CH=CH-$, $-CH_2CH_2CH_2-$ or $-CH=CHCH_2-$; and when one or other of them is substituted with one or more oxo or thio groups it may be any of the groups (b): $-CH_2CO-$, $-CH_2CH_2CO-$, $-CH=CHCO-$, $-CO.CO-$, $-CO.CH_2CO-$ (this being tautomeric with $-CO.CH=C(OH)-$), $-CO.CO.CO-$ or the corresponding thio-carbonyl groups. When X or Y are substituted with one or more halogen atoms or lower alkyl or phenyl groups, such halogen or lower alkyl or phenyl replaces hydrogen in the groups (a) or (b).

Some of the compounds of formula I are known from the chemical literature, the unsubstituted compounds in which R and Z are hydrogen, X is trimethylene and Y is ethylene or trimethylene being known as lilolidine and julolidine, respectively, and oxo-derivatives thereof being known as lilolidones and julolidones, respectively. However, no compound of the formula I has ever been proposed for use in the treatment or control of plant diseases. Moreover, particular classes of compounds of the formula I are novel and have been found to be useful in accordance with the present invention.

According to one aspect of the present invention, therefore, there is provided a novel composition for the treatment of plant diseases which comprises a compound of the formula I, together with a diluent or carrier material which is compatible with the intended use of the composition.

The compositions of the invention may comprise a diluent or carrier, liquid or solid, in the form of sprays, including emulsions, slurries and solutions, dusts, foams, or granules. When applied to rice plants the compositions preferably take the form of sprays of solutions, slurries or emulsions containing compounds of the formula I at a total volume of spray of from about 100 liters to about 600 liters per acre. The concentration of active ingredient in the spray can range from about 5 to about 500 parts per million (ppm).

Application at these levels is sufficient to achieve run-off and achieves substantially complete contact of the surface of the rice plant with the active ingredient. The use of a water-insoluble form of the active ingredient is preferred for foliar sprays, rather than a water-soluble form, to avoid their removal from the plants by rain or flooding.

For convenience and economy of application the compositions of the invention may consist of the active ingredient formulated into a dust, wettable powder or emulsifiable concentrate. A dust may be made by mixing the proper amount of active ingredient with a diluent or carrier such as talc, clay, calcite, pyrophyllite, diatomaceous earth, walnut shell flour, silica gel, hydrated alumina, calcium silicate, or mixtures thereof to afford a concentration of active ingredient of from about 0.25 per cent to about 4 percent by weight. A dust can also be prepared by mixing the diluent or carrier with a solution of the active ingredient in a volatile organic solvent such as benzene or acetone. The solvent is then removed by evaporation and the mixture ground. Additives to improve the flowability of the dusts may also be added.

Wettable powders, of special value for spray applications, may be made by adding suitable wetting agents and conditioning agents to the dusts.

Emulsifiable concentrates may be made by dissolving the active ingredient and an emulsifying agent in a substantially water-immiscible organic solvent. Suitable solvents are toluene, xylene and petroleum oil or an alkylated naphthalene. The volatile solvents, e.g. toluene, xylene, evaporate after spraying to leave a deposit of the active ingredient upon the plant. The nonvolatile solvents leave an oily solution of the active ingredient upon the plant. The emulsifying agent can be cationic, anionic, or non-ionic as is well known to those skilled in the art. As suitable emulsifiers there may be mentioned ordinary soaps (anionic), lauryl pyridinium chloride (cationic) and polyoxyethylene lauryl ethers (non-ionic), the latter being for example a reaction product of ethylene oxide (ten moles) with dodecylalcohol (one mole). Such concentrates may suitably contain from 2 to 50 percent of the active ingredient and may be mixed with a sufficient volume of water to provide a concentration of active ingredient of from 5 to 500 ppm. For the present purpose, the resulting emulsion may be applied at a rate of from about 100 to 600 liters per acre.

If a water soluble form of the active ingredient is used, it is most conveniently applied in the form of an aqueous spray. Here also, the rate of application is suitable from about 100 to 600 liters per acre of a solution containing 5 to 500 ppm of active ingredient.

The compositions of the invention may also be applied indirectly by adding them to the water in which the plant is growing. One convenient form for this application is as granules, by means of which time release of the active ingredient may be controlled.

Compositions of the invention can also be used as seed dressings. When used for the treatment of seeds the prepared forms of the compositions may be dusts, solutions, slurried or emulsions which are applied directly to the seed by appropriate means as by tumbling with the dust or mixing in the solution. For seed protection, levels of active ingredient similar to those previously mentioned are used, e.g. 5 to 500 ppm. of active ingredient in solutions, emulsions, sprays and 0.25 percent to 4 percent in dusts.

Another useful form in which the compositions of this invention may be used is as foams. This form of application prevents drift of the active ingredients from one field to another where such treatment may not be desired.

For the compositions of the invention, a wide choice of diluents, emulsifiers, wetting agent or solvents, is available. The particular diluent, emulsifier, solvent or wetting agent best suited for a given formulation may readily be determined by those skilled in the art by simple experiment.

Preferred compositions according to the invention are those which comprise a compound of formula I in which either X or Y is substituted with a single oxo or thio group, in a position adjacent to the ring nitrogen atom, and R is either hydrogen or a halogen, lower alkyl or lower aliphatic acyl substituent in the para-position to the ring nitrogen atom and Z is hydrogen. Particularly preferred are those compositions comprising a compound in which X is $-CH_2CO-$, $-CH_2CH_2CO$, $-CH{=}CHCO-$, or a corresponding thio-carbonyl group (the $-CO-$ or $-CS-$ group being adjacent to the ring nitrogen atom), each being optionally substituted with one or more lower alkyl or phenyl groups, and Y is $-CH_2CH_2-$ or $-CH_2CH_2CH_2-$, i.e. a compound of the formulae:

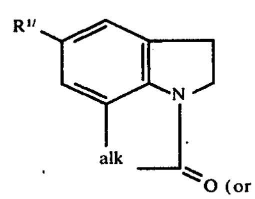

or

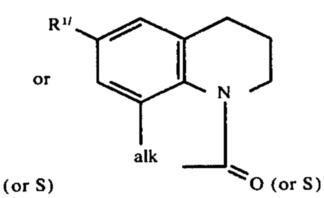

IA IB where $R^{1\prime}$ is hydrogen, halogen, lower alkyl, lower alkoxy or lower aliphatic acyl and "alk" represents a methylene, ethylene or vinylene group, either of which may be substituted with one or more lower alkyl or phenyl groups.

According to another aspect of the invention, there are provided novel pyrrolo-[3,2,1-i,j]-quinolines of the formula:

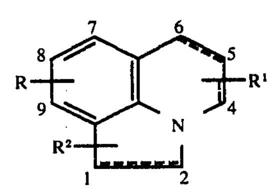

II where R is as previously defined other than hydrogen, $R^1$ and $R^2$ each represent hydrogen or one or more halogen, lower alkyl, phenyl, oxo or thio substituents in the pyrido and pyrrolo rings respectively, and the dotted lines represent an optional bond in each such ring.

Also according to this aspect of the invention, there are provided novel pyrido-[3,2,1-i,j]-quinolines of the formula:

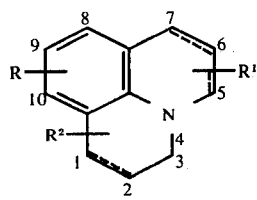

III where R is as previously defined other than hydrogen or 9-chloro, $R^1$ and $R^2$ each represent hydrogen or substituents (as previously defined) in the respective pyrido rings and the dotted lines represent an optional bond in each such ring.

Also included in the invention are the non-phytotoxic acid addition salts of those compounds which form acid addition salts.

One class of preferred novel compounds of the invention are those of the formula II, in which either $R^1$ or $R^2$ includes a single oxo or thio group in a position adjacent to the ring nitrogen atom, and R is halogen or a lower alkyl, lower alkoxy or lower alkanoyl group in the 8-position. Particularly preferred compounds of this class are those of the formulae:

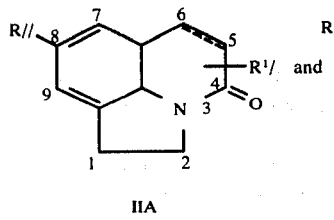 and 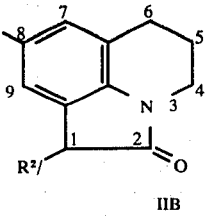

IIA                                    IIB where R'' is halogen or a lower alkyl, lower alkoxy or lower alkanoyl group, and $R^{1\prime}$ and $R^{2\prime}$ are each hydrogen or one or more lower alkyl groups.

Another class of preferred novel compounds of the invention are those of the formula III in which R is a lower alkyl, lower alkoxy or lower alkanoyl in the 9-position. Particularly preferred compounds of this class are those of the formula:

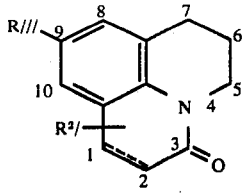

IIIA where R''' is a lower alkyl, lower alkoxy or lower alkanoyl group, and $R^{2\prime}$ is hydrogen or represents one or more lower alkyl groups or a 1-oxo group and an optional 2-phenyl or 2-lower alkyl group.

In this specification, "lower" when applied to an alkyl, alkoxy, alkanoyl or alkanoyloxy group means that such a group contains up to four carbon atoms. Thus, when R, R', R'' or R''' in formulae I to IIIA, or $R^1$, $R^{1\prime}$, $R^2$, or $R^{2\prime}$ in formulae II to IIIA, is or includes a lower alkyl group, that group may, for example, be a methyl, ethyl, propyl, isopropyl, n-butyl, iso-butyl, sec-butyl or tert-butyl group, and when R, R', R'' or R''' in formulae I to IIIA is a lower alkoxy group it may, for example, be a methoxy group or any other alkoxy group containing up to four carbon atoms. When R, R', R'' or R''' in formulae I to IIL is a lower alkanoyl or alkanoyloxy group it may, for example, be a formyl, acetyl, propionyl, butyryl or isobutyryl group or a corresponding acyloxy group.

Compounds of the formulae I to IIIA which form acid addition salts include those in which there is no oxo or thio group adjacent to the ring nitrogen atom, but are not limited to such compounds. Non-phytotoxic acid addition salts are those which are formed with acids having non-phytotoxic anions, for example, the hydrochloride hydrobromide, phosphate, nitrate, sulfate, acetate, β,β-dimethylbutyrate, citrate, gluconate, benzoate, propionate, butyrate, sulfo-salicylate, maleate, laurate, malate, fumarate, succinate, oxalate, tartrate, amsonate (4,4'-diamino-stilbene-2,2'-disulfonate), pamoate (1,1'-methylene-bis-2-hydroxy-3-naphthoate), stearate, 2-hydroxy-3-naphthoate and p-toluene-sulfonate salts.

Also provided by the invention are the novel compounds lilolidine-2-thione, lilolidine-4-thione, julolidine-3-thione, 8-acetyl-4-lilolidone, and 8-benzoyl-2-lilolidone.

A preferred method of treating diseases of plants is that in which the plants are contacted with compounds of formula I in which: one of X and Y is substituted with a single oxo or thio group in a position adjacent to the ring nitrogen atom, R is hydrogen, halo, lower alkyl or lower aliphatic acyl para to the ring nitrogen atom; and Z is hydrogen.

In another such preferred method: X is —CH$_2$CO—, —CH$_2$CH$_2$CO—, —CH=CHCO— or a corresponding thio-carbonyl group, the —CO— or —CS— group being adjacent to the ring nitrogen atom, each being optionally substituted with up to two substituents selected from lower alkyl or phenyl, Y is —CH$_2$CH$_2$— or —CH$_2$CH$_2$CH$_2$—, R is hydrogen, halo, lower alkyl, lower alkoxy or lower alkanoyl para to the ring nitrogen, and Z is hydrogen.

Pyrrolo [3,2,1-i,j]-quinolines of the formula:

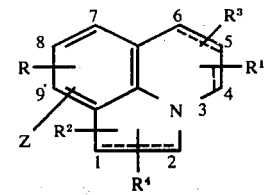

wherein
R is lower alkyl, lower alkoxy, lower alkanoyl, benzoyl, hydroxy, lower alkanoyloxy, cyano, halo;
Z is hydrogen or halo;
$R^1$, $R^2$, $R^3$ and $R^4$ are each hydrogen, halogen, lower alkyl, phenyl, oxo or thio; and the dotted lines represent an optional bond in each such ring;

and the non-phytotoxic acid addition salts of those compounds which form acid addition salts are preferred novel compounds.

Especially preferred are compounds in which one of $R^1$ and $R^2$ is oxo or thio adjacent to the ring nitrogen, R is halo, lower alkyl, lower alkoxy, or lower alkanoyl in the 8-position; and Z is hydrogen.

Other preferred compounds are:

Pyrido-[3,2,1-i,j]-quinolines of the formula:

wherein
R is lower alkyl, lower alkoxy, lower alkanoyl, benzoyl, hydroxy, lower alkanoyloxy, cyano or halo;
Z is hydrogen or halo, provided that when Z is hydrogen, R is other than 9-chloro;
$R^1$, $R^2$, $R^3$ and $R^4$ are each hydrogen, halo, lower alkyl, phenyl, oxo or thio;
and the dotted lines represent an optional bond in each such ring;
and the non-phtotoxic acid addition salts of those compounds which form acid addition salts.

Especially preferred are compounds of the formulae:

wherein R is lower alkyl, lower alkoxy or lower alkanoyl;
$R^2$ and $R^4$ are each hydrogen or lower alkyl;
and the dotted line represents an optional 1,2-bond.
and wherein R is lower alkyl, lower alkoxy or lower alkanoyl; and $R^2$ is hydrogen, phenyl or lower alkyl.

The present invention may be used to treat or control fungal and/or bacterial diseases of plants, particularly (but not limited to) diseases of the rice plant, including the fungal diseases known as rice blast (caused by *Piricularia oryzoe*) and leaf blight (caused by *Xanthomonas oryzae*), and the bacterial disease known as sheath blight (caused by *Corticium sasakii*). Other plants, for which the present invention may be used to treat or control fungal or bacterial disease, include tomato and cucumber plants.

DETAILED DESCRIPTION OF THE INVENTION

The novel compounds of the invention as well as the known compounds may be prepared by a number of methods, including the following:

1. An indole or quinoline compound of the formula:

where R and $R^1$ are as previously defined, with the provisos that R cannot be a substituent in the 7-position of the indole ring or the 8-position of the quinoline ring and cannot be a substituent of such a nature as to deactivate that position or be an acylatable group, and $R^1$ does not include an oxo or thio substituent, may be reacted with a chloro-substituted acid chloride of the formula Cl-alk-COCl, in which "alk" is a methylene, ethylene or vinylene group which may be substituted with one or more lower alkyl or phenyl groups, in the presence of a base, e.g. trimethylamine, to form a compound of the formula:

which is then cyclized in the presence of aluminium chloride to form a compound of the formula II or III, in which $R^1$ does not include an oxo or thio substituent, but $R^2$ includes an oxo substituent adjacent to the ring nitrogen atom and may also include one or more lower alkyl or phenyl substituents. If in this method R includes any alkoxy group, such group is converted under the conditions of cyclization to a hydroxyl group.

2. A quinoline compound of the formula:

where R and $R^1$ are as defined for method (1), may be reacted with acrylonitrile or a β-halo-propionitrile of the formula $XCH_2CH_2CN$ (in which X is halogen) to form a compound of the formula:

which is hydrolyzed to convert the nitrile group to a carboxy group and then cyclized in the presence of a dehydrating agent, e.g. phosphoric anhydride, to form a compound of formula III in which $R^2$ is 1-oxo and $R^1$ does not include an oxo or thio substituent.

3. An aniline derivative of the formula:

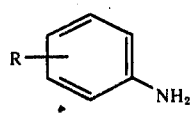

where R is as previously defined, with the provisos that it cannot be a substituent in the 2- or 6-position of the benzene ring and cannot be a substituent of such a nature as to de-activate either of these positions or be an acylatable group, may be reacted with 2 moles of acrylonitrile or a β-halo-propionitrile as defined in method (2) to form a compound of the formula:

which is then hydrolyzed and cyclized as in method (2) to form a compound of formula III in which $R^1$ is 6-oxo and $R^2$ is 1-oxo.

4. A compound of the formula:

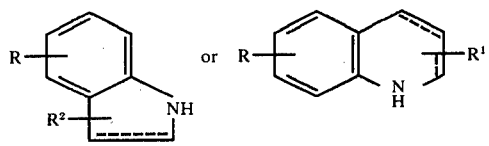

where R and $R^1$ are as defined for methods (1) or (2) and $R^2$ is as previously defined with the proviso that it does not include an oxo or thio substituent, may be reacted with an aceto-acetic acid ester of the formula $R^5COCHR^6COOC_2H_5$, in which $R^5$ is a lower alkyl or phenyl group and $R^6$ is hydrogen or a lower alkyl group, to form a compound of the formula:

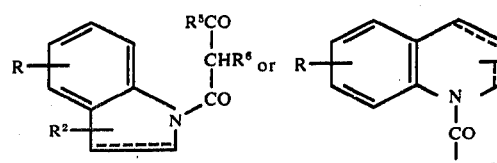

which is then cyclised in the presence of a dehydrating agent, e.g. concentrated sulphuric acid or polyphosphoric acid, to form a compound of the formula:

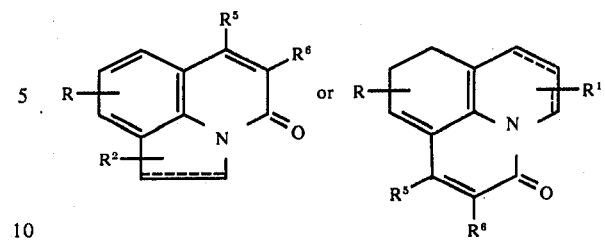

5. A compound of the formula:

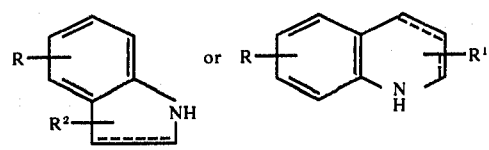

where R, $R^1$ and $R^2$ are as defined for methods (1), (2) or (3), is reacted with a malonic acid ester of the formula:

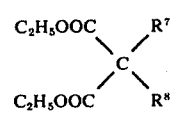

in which $R^7$ and $R^8$ are each hydrogen or a lower alkyl or phenyl group, to form a compound of the formula:

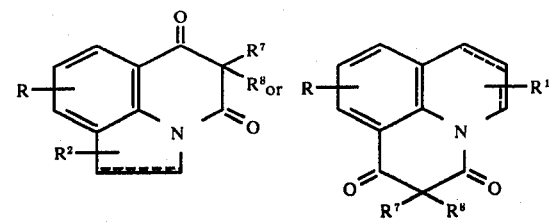

which, in the case where $R^7$ is hydrogen, are tautomeric with the formulae:

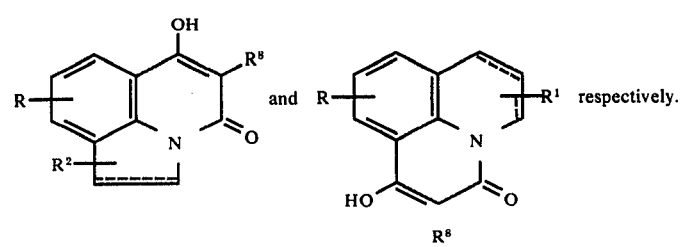

and respectively.

6. A compound of the formula II or III, in which $R^1$ and/or $R^2$ includes one or more oxo substituents, may be reduced with lithium aluminium hydride to replace the oxo substituent(s) with hydrogen.

7. A compound of the formula II or III, in which $R^1$ and/or $R^2$ includes one or more oxo substituents, may be treated with diphosphorus pentasulphide to replace the oxo substituent(s) with sulphur.

8. A compound of formula I, in which X or Y includes an unsaturated group, may be converted to the corresponding saturated compounds by catalytic hydrogenation, which may also result in replacement of halogen substituents in X or Y by hydrogen.

9. A compound of the formula I, in which R and Z are each hydrogen, may be converted to a compound of the same formula, but in which R is halogen, alkyl, alkanoyl or benzoyl, or in which R and Z are each halogen, by well-known techniques of nuclear aromatic halogenation, alkylation or acylation, respectively, and R may then be converted to other groups by well-known reaction sequences, including (for example) replacement of halogen by cyano.

Aromatic halogenation, e.g. chlorination with gaseous chlorine or with dichlorourethane, may also result in the introduction of halogen into $R^1$ and $R^2$, especially at positions adjacent to any oxo group(s). Such halogen may subsequently be removed, if not required, by selective reduction to replace it by hydrogen, converted to other groups, e.g. to an oxo group by hydrolysis of a gem-dihalo group, or replaced by phenyl by Friedel-Crafts reaction with benzene.

10. A compound of the formula I, in which R includes one or more hydroxyl groups, may be converted to lower aliphatic acyl esters thereof by conventional esterification techniques.

11. Compounds of the formula II or III, in which $R^1$ or $R^2$ includes one or more halogen substituents, may also be formed from the corresponding hydroxy compounds by conventional methods for the conversion of alcohols to halides, e.g. treatment with phosphorus or thionyl halides. The hydroxy compound starting materials may, for example, be the enolic forms of β-diketones, i.e. compounds in which $R^1$ or $R^2$ includes two ozo substituents separated by a methylene group, which may be substituted by an alkyl or phenyl group.

12. Non-phytotoxic acid addition salts of any compound of the formula I, which is sufficiently basic to form such salts, may be formed by conventional methods, e.g. by dissolving the compound in a suitable solvent and adding the appropriate acid, either in a solvent also, or as the acid itself if liquid or gaseous, to precipitate the required salt.

The invention is illustrated by the following Examples, in which temperatures are given in ° C.

EXAMPLE 1

A. To a stirred solution of 6-methyl-1,2,3,4-tetrahydroquinoline (7.4 g) in dry benzene (120 ml) containing triethylamine (8.4 ml) was added over a period of ½ hour chloroacetyl chloride (6.0 g, 4.3 ml). Stirring was continued for a further 2 hours, after which the precipitate of triethylamine hydrochloride was filtered off and the benzene filtrate was washed in turn with 2N hydrochloric acid (100 ml) and water (2 × 100 ml). The benzene solution was then dried over anhydrous magnesium sulphate and evaporated in vacuo to afford a gum (9.5 g), most of which was used directly in the next stage (B).

A portion (3.5 g) of the aforementioned gum was purified by passage through a silica column using chloroform as the eluent, and the chloroform solution was evaporated in vacuo to an oil which eventually solidified. A sample was recrystallised from petroleum ether (b.p. 40°–60°) to yield a solid, m.p. 58°–60°, shown by standard analytical techniques to be 1-chloroacetyl-6-methyl-1,2,3,4-tetrahydroquinoline.

Analysis:
Found: C, 64.09; H, 6.26; N, 6.22%. Calculated for $C_{12}H_{14}NOCl$: C, 64.46; H, 6.27; N, 6.27%

B. The gummy product of the previous stage (6.0 g) and finely powdered anhydrous aluminium chloride (5.0 g) were mixed at room temperature, whereupon the temperature of the mixture rose to about 130°. The mixture was then warmed in an oil both at 140° for 30 minutes (during which time the temperature within the mixture rose to 170°) and thereafter poured while still hot onto a mixture of ice and hydrochloric acid. Extraction of the aqueous solution with chloroform (2 × 50 ml) was followed by washing the organic solution with water and drying over anhydrous magnesium sulphate. Evaporation of the chloroform layer in vacuo afforded an oil (3.7 g) which solidified. The crude solid product was recrystallised from petroleum ether (b.p. 60°–80°) to yield 1.6 g of 8-methyl-1,2,5,6-tetrahydro-4H-pyrrolo-[3,2,1-i,j]-quinolin-2-one, m.p. 115°–7°.

Analysis:
Found: c, 77.01; H, 6.93; N, 7.47%. Calculated for $C_{12}H_{13}NO$: C, 77.01; H, 6.95; N, 7.49%

EXAMPLES 2 to 4

By procedures similar to that described in Example 1, the following novel compounds were prepared starting from the appropriate substituted 1,2,3,4-tetrahydroquinoline and chloroacyl chloride.

Similarly the known compounds 1,2,5,6-tetrahydro 4H-pyrrolo-[3,2,1-ij]-quinoline-2-one (2-lilolidone), and its 1-phenyl and 1-methyl derivatives, were prepared from 1,2,3,4-tetrahydroquinoline and chloracetyl chloride, α-chloro-phenylacetyl chloride and α-chloropropionyl chloride respectively; and the known compound 1,2,5,6-tetrahydro-4H-pyrrolo-[3,2,1-i,j]-quinolin-4-one (4-lilolidone) was prepared from indoline and β-chloropropionyl chloride.

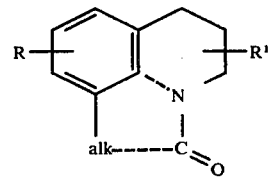

| Example | R | $R^1$ | alk | m.p. ° C | Analysis (theoretical in brackets) | | |
|---|---|---|---|---|---|---|---|
| | | | | | C % | H % | N % |
| 2 | 9-$CH_3$ | H | —$CH_2$—$CH_2$— | 63–5° | 77.32 (77.58 | 7.46 7.57 | 6.62 6.96) |

-continued

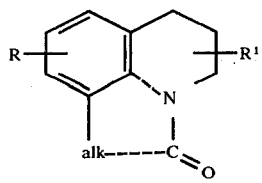

| Example | R | R¹ | alk | m.p. °C | Analysis (theoretical in brackets) C % | H % | N % |
|---------|------|------|------------|--------|----------------|------|------|
| 3 | 8-CH₃ | 1-H | —CH—<br>\|<br>Ph | 80–81° | 82.22<br>(82.20 | 6.52<br>6.47 | 5.66<br>5.33) |
| 4 | H | 4-CH₃ | —CH₂— | 65–7° | (77.01 | 6.95 | 7.49) |

EXAMPLE 5

Chlorine was passed into a solution of 1,2,5,6-tetrahydro-4H-pyrrolo-[3,2,1-i,j]-quinolin-2-one (5.0 g) in chloroform (50 ml) for a period of 20 minutes, and the resultant pale orange solution was then concentrated by evaporation in vacuo to an oil. A small sample was crystallised by trituration in petroleum ether, and the crystals were used as seeds to bring about total crystallisation of the oil. The crystalline solid was re-crystallised from a mixture of benzene and petroleum ether, yielding 1,1,8-trichloro-1,2,5,6-tetrahydro-4H-pyrrolo-[3,2,1-i,j]-quinolin-2-one, m.p. 148°–9°.
Analysis:
Found: C, 47.30; H, 2.76; N, 5.03%. Calculated for $C_{11}H_8Cl_3NO$: C, 47.70; H, 2.90; N, 5.07%.

EXAMPLE 6

1,2,5,6-Tetrahydro-4H-pyrrolo-[3,2,1-i,j]-quinolin-2-one (5 g) was dissolved in 80% acetic acid and dichlorourethane (4.5 g, 5.5 ml) was added whereupon the temperature of the solution was observed to rise to about 60°. The solution was stirred for 4 hours after which water (10 ml) was added, resulting after a few minutes in the precipitation of a white powder. The latter was collected by filtration and recrystallised in turn from glacial acetic acid and a mixture of benzene and petroleum ether, yielding what was believed from infra-red and nuclear magnetic resonance spectroscopic evidence to be 1,1,7,8-tetrachloro-1,2,5,6-tetrahydro-4H-pyrrolo-[3,2,1-i,j]-quinolin-2-one, m.p. 167°–170°.
Analysis:
Found: C, 43.29; H, 2.61; N, 4.66%. Calculated for $C_{11}H_7Cl_4NO$: C, 42.50; H, 2.27; N, 4.51%.

EXAMPLE 7

To a solution of 1,2,5,6-tetrahydro-4H-pyrrolo-[3,2,1-i,j]-quinolin-4-one (1.0 g) in carbon tetrachloride (20 ml) was added a solution of bromine (0.35 ml) in the same solvent (5 ml). After a few minutes a solid separated, and this was filtered off and recrystallised from a mixture of water and methanol to afford 0.75 g of 8-bromo-1,2,5,6-tetrahydro-4H-pyrrolo-[3,2,1-i,j]-quinolin-4-one, m.p. 107°14 9°.
Analysis:
Found: C, 52,36; H, 4.00; N, 5.66%. Calculated for $C_{11}H_{10}BrNO$: C, 52.40; H, 4.00; N, 5.50%.

EXAMPLE 8

A solution of 1,2,5,6-tetrahydro-4H-pyrrolo-[3,2,1-i,j]-quinolin-2-one (5.0 g) and bromine (1.5 ml) in chloroform (15 ml) was warmed to 45° and maintained at that temperature. Within 5 minutes a precipitate had formed and this was collected by filtration and recrystallised from 75% aqueous acetic acid solution, yielding 8-bromo-1,2,5,6-tetrahydro-4H-pyrrolo-[3,2,1-i,j]-quinolin-2-one, m.p. 125°–6°.
Analysis:
Found: C, 53.09; H, 4.02; N, 5.59%. Calculated for $C_{11}H_{10}BrNO$: C, 52.30; H, 3.99; N, 5.56%.

EXAMPLE 9

A solution of bromine in chloroform (1 ml taken from 5.52 ml in 10 ml) was slowly added to a solution of 1-phenyl-1,2,5,6-tetrahydro-4H-pyrrolo-[3,2,1-i,j]-quinolin-2-one (2.49 g) in chloroform (50 ml) whereupon an exothermic reaction ensued with evolution of hydrogen bromide. The mixture was warmed for ½ hour on a steam bath after which the solution was evaporated to dryness in vacuo and a portion of the solid was submitted to nuclear magnetic resonance spectroscopy. The evidence suggested incomplete reaction, and so more bromine in chloroform solution was added to a solution of the residue in chloroform with warming and the reaction allowed to continue for a further short period of time.
The solution was evaporated in vacuo and the solid residue recrystallised from a mixture of cyclohexane and petroleum ether, affording 1,8-dibromo-1-phenyl-1,2,5,6-tetrahydro-4H-pyrrolo-[3,2,1-i,j]-quinolin-2-one, m.p. 119.5°–120.5°.
Analysis:
Found: C, 51.04; H, 3.50; N, 3.41%. Calculated for $C_{17}H_{13}NOBr_2$: C, 50.15; H, 3.22; N, 3.44%.

EXAMPLE 10

By a procedure similar to that described in Example 9, 1,8-dibromo-1-methyl-1,2,5,6-tetrahydro-4H-pyrrolo-[3,2,1-i,j]-quinolin-2-one, m.p. 138°–9°, was prepared by bromination of 1-methyl-1,2,5,6-tetrahydro-4H-pyrrolo-[3,2,1-i,j]-quinolin-2-one.
Analysis:
Found: C, 42.14; H, 3.58; N, 4.00%. Calculated for $C_{12}H_{11}NOBr_2$: C, 41.77; H, 3.21; N, 4.06%.

EXAMPLE 11

To a solution of 1,2,5,6-tetrahydro-4H-pyrrolo-[3,2,1-i,j]-quinolin-2-one (10 g) in chloroform (30 ml) was added bromine (3.1 ml), after which the solution was allowed to stand at room temperature. Within a few minutes a precipitate had formed, and this was filtered off, washed with chloroform and dried, the yield of 8-bromo-compound being 10 g.

The 8-bromo-1,2,5,6-tetrahydro-4H-pyrrolo-[3,2,1-i,j]-quinolin-2-one (10 g) was suspended in chloroform and chlorine was bubbled into the suspension, whereupon dissolution rapidly occurred. Chlorine passage was continued for about 20 minutes after which the solution was evaporated in vacuo and the resulting gummy solid was triturated in petroleum ether. Recrystallisation of the resultant solid afforded 8-bromo-1,1-dichloro-1,2,5,6,-tetrahydro-4H-pyrrolo-[3,2,1-i,j]-quinolin-2one, buff coloured crystals, m.p. 149–150°.

Analysis:
Found: C, 40.96; H, 2.57; N, 4.32%. Calculated for $C_{11}H_8BrCl_2NO$: C, 41.10; H, 2.51; N, 4.36%.

EXAMPLE 12

A mixture of 1,2,5,6-tetrahydro-4H-pyrrolo-[3,2,1-i,j]-quinolin-4-one (1.0 g), propionic acid (1.0 ml) and polyphosphoric acid (phosphorus pentoxide content 82–5%, 80 g) was heated on a steam bath for 3 hours and then poured while still hot into water. The mixture was then stirred until appearing homogeneous and extracted with diethyl ether (2 × 100 ml), the ethereal layer then being separated, washed with water, dried over anhydrous magnesium sulphate and evaporated in vacuo to dryness. Crystallisation of the resultant solid from ethanol afforded 0.45 g of 8-propionyl-1,2,5,6-tetrahydro-4H-pyrrolo-[3,2,1-i,j]-quinolin-4-one, m.p. 144°–7°.

Analysis:
Found: C, 73.34; H, 6.59; N, 6.11%. Calculated for $C_{14}H_{15}NO_2$: C, 73.67; H, 6.47; N, 5.89%.

EXAMPLES 13 to 19

By procedures similar to that described in Example 12, the compounds of Examples 13 to 16 were prepared by acylations with appropriate carboxylic acids of appropriately substituted or unsubstituted 1,2,5,6-tetrahydro-4H-pyrrolo-[3,2,1-i,j]-quinolinones in the presence of polyphosphoric acid. The compound of Example 19 was prepared by the benzoylation of 1,2,5,6-tetrahydro-4H-pyrrolo-[3,2,1-i,j]-quinolin-2-one under similar dehydrating conditions.

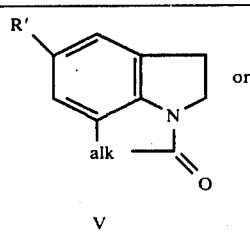 or 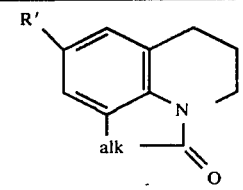

V                                         VI

| Example | Formula | alk | R' | m.p. °C | Analysis (theoretical in brackets) C % | H % | N % |
|---|---|---|---|---|---|---|---|
| 13 | VI | —CH—<br>\|<br>CH₃ | $C_2H_5CO$— | 115–6° | 73.00<br>(72.73 | 7.06<br>7.12 | 5.56<br>5.65) |
|  |  |  |  |  | (based on $C_{15}H_{17}NO_2 \cdot \tfrac{1}{4}H_2O$) |  |  |
| 14 | VI | —CH—<br>\|<br>CH₃ | $CH_3(CH_2)_2CO$— | 102–4° | 74.52<br>(74.68 | 7.40<br>7.44 | 5.69<br>5.44) |
| 15 | VI | —CH₂— | $CH_3CO$— | 154–6° | 72.33<br>(72.50 | 6.14<br>6.05 | 6.46<br>6.52) |
| 16 | VI | —CH₂— | $C_2H_5CO$— | 169–170° | 73.99<br>(73.34 | 6.26<br>6.59 | 5.86<br>6.11) |
| 17 | V | —CH₂—CH₂— | $CH_3CO$— | 97–100° | 71.77<br>(72.50 | 6.07<br>6.05 | 3.87<br>6.52) |
| 18 | VI | —CH—<br>\|<br>CH₃ | $CH_3CO$— | 113–5° | 73.46<br>(73.34 | 6.68<br>6.59 | 6.10<br>6.11) |
| 19 | VI | —CH₂— | $C_6H_5CO$— | 127–130° | 77.17<br>(76.96 | 5.31<br>5.70 | 5.24<br>5.28) |

EXAMPLE 20

To a suspension of 1,1,8-trichloro-1,2,5,6-tetrahydro-4H-pyrrolo-[3,2,1-i,j]-quinolin-2-one (prepared as in Example 5) (2.0 g) in 50% aqueous methanol (100 ml) contained in a bomb was added anhydrous sodium acetate (0.5 g). The suspension was heated for 24 hours at 100°. The resulting dark red solution containing a little undissolved material was freed of the latter by filtration and concentrated by evaporation in vacuo. A solid precipitate was collected by filtration and recrystallised from a mixture of benzene and petroleum ether, affording deep red crystals of 8-chloro-1,2,5,6-tetrahydro-4H-pyrrolo-[3,2,1-i,j]-quinolin-1,2-dione, m.p. 185°.

Analysis:

Found: C, 59.7; H, 3.66; N, 6.17%. Calculated for $C_{11}H_8ClNO_2$: C, 59.45; H, 3.64; N, 6.32%.

EXAMPLE 21

By a procedure similar to that described in the previous Example, 8-bromo-1,1-dichloro-1,2,5,6-tetrahydro-4H-pyrrolo-[3,2,1-i,j]-quinolin-2-one (prepared as in Example 11) was hydrolysed and yielded 8-bromo-1,2,5,6-tetrahydro-4H-pyrrolo-[3,2,1,-i,j]-quinolin-1,2-dione, as dark red crystals, m.p. 185°–7°.

Analysis:
Found: C, 49.90; H, 3.10; N, 5.42%. Calculated for $C_{11}H_8BrNO_2$: C, 49.60; H, 3.30; N, 5.27%.

EXAMPLE 22

To a stirred suspension of 1,1,8-trichloro-1,2,5,6-tetrahydro-4H-pyrrolo-[3,2,1-i,j]-quinolin-2-one (prepared as in Example 5) (5 g) in acetic acid (100 ml) was added zinc dust (5 g) at such a rate as to keep the temperture of the mixture below 50°. After complete addition of zinc, the mixture was refluxed with stirring for 5 hours. The supernatant liquid was decanted into water whereupon a solid precipitated. The precipitate was collected by filtration, recrystallised from cyclohexane and dried in vacuo, yielding 2 g of 8-chloro-1,2,5,6-tetrahydro-4H-pyrrolo-[3,2,1-i,j]-quinolin-2-one, m.p. 120°–2°.

Analysis:
Found: C, 63.60; H, 5.13; H, 6.74%. Calculated for $C_{11}H_{10}ClNO$: C, 63.70; H, 4.88; N, 6.75%.

EXAMPLE 23

To a solution of 1,1,8-trichloro-1,2,5,6-tetrahydro-4H-pyrrolo-[3,2,1-i,j]-quinolin-2-one (prepared as in Example 5) (4.5 g) in dry benzene (100 ml) was added aluminium chloride (4.3 g), and the mixture was then heated, gently at first, to reflux whereafter refluxing was continued for 2 hours. Throughout this period hydrogen chloride was evolved.

The mixture was then allowed to cool to room temperature, poured into water and the resultant solid filtered, washed with diethyl ether and crystallised from benzene, affording crystals, m.p. 265°–7°. A second crop of crystals was produced on addition of petroleum ether to the benzene filtrate, and this was collected by filtration. Both crops were seen to be pure from thin layer chromatography evidence and so were combined, and constituted the total yield of 8-chloro-1,1-diphenyl-1,2,5,6-tetrahydro-4H-pyrrolo-[3,2,1-i,j]-quinolin-2-one.

Analysis:
Found: C, 76.53; H, 5.39; N, 3.45%. Calculated for $C_{23}H_{18}ClNO$: C, 76.80; H, 5.04; N, 3.89%.

EXAMPLE 24

A mixture of 1,2,5,6-tetrahydro-4H-pyrrolo-[3,2,1-i,j]-quinolin-2-one (1.73 g), tert-butyl chloride (5 ml) and aluminium chloride (~0.5 g) was heated at about 60° for 2 hours, at the end which period the whole had virtually solidified. It was then added to water and the suspension was extracted with chloroform, the chloroform solution then being separated, dried over anhydrous magnesium sulphate and evaporated in vacuo to dryness. The solid was recrystallised from 60°–80° petroleum ether and submitted to gas liquid chromatography, the evidence suggesting that there was present a mixture of 1,2,5,6-tetrahydro-4H-pyrrolo-[3,2,1-i,j]-quinolin-2-one and its 8-tert-butyl derivative.

Dissolution of the solid in hot petroleum mixture and subsequent cooling resulted in precipitation of a solid, believed to be an impurity. The precipitate was removed by filtration and the filtrate evaporated in vacuo to dryness, the resultant solid then being submitted to gas liquid chromatography, the evidence from which suggesting a ~96% pure product. Standard analytical techniques confirmed that this product was 8-tert-butyl-1,2,5,6-tetrahydro-4H-pyrrolo-[3,2,1-i,j]-quinolin-2-one, m.p. 122°–4°.

Analysis:
Found: C, 80.09; H, 8.10; N, 5.86%. Calculated for $C_{15}H_{19}NO$: C, 78.90; H, 8.30; N, 6.12%.

EXAMPLE 25

A. To a stirred solution of 6-methoxy-1,2,3,4-tetrahydroquinoline (4.02 g) and triethylamine (3.0 g) in dry benzene (80 ml) was added dropwise over 30 minutes chloroacetyl chloride (2.82 g). Stirring was continued for a further 3 hours at room temperature, after which the triethylamine hydrochloride in suspension was removed by filtration and the benzene solution filtrate was washed in turn with 2N hydrochloric acid and water, and then dried over anhydrous magnesium sulphate. Evaporation of the benzene solution in vacuo afforded an oil (4.0 g) which could not be crystallised, and so it was used directly as such in the next stage. The product in crude form was 1-chloroacetyl-6-methoxy-1,2,3,4-tetrahydroquinoline. The procedure was repeated to obtain a further quantity of the crude product.

B. The product of (A) (9.0 g) was mixed with powdered anhydrous aluminium chloride (18.0 g) and the mixture was gradually heated to 100°, fumes of hydrogen chloride being evolved, and heating was continued until and oil-bath temperature of 200° had been attained, at which point the mixture was a molten mass. The reaction mixture was heated for a further 1 hour at an oil-bath temperature of 200°, and then cooled to room temperature, the mixture by then having solidified. The ground mixture was added to an ice-water mixture, and the aqueous solution then extracted with chloroform, the chloroform solution then being extracted with sodium hydroxide solution. On standing, the latter afforded a precipitate, and the suspension was extracted with fresh chloroform. The chloroform solution was dried over anhydrous magnesium sulphate and evaporated to dryness in vacuo, the resultant solid (3.5 g) then being recrystallised from absolute ethanol to afford 8-hydroxy-1,2,5,6-tetrahydro-4H-pyrrolo-[3,2,1i,j]-quinolin-2-one, m.p. 200°–202°.

Analysis:
Found: C, 69.09; H, 5.96; N, 7.44%. Calculated for $C_{11}H_{11}NO_2$: C, 69.82; H, 5.86; N, 7.40%.

EXAMPLES 26 and 27

By procedures similar to that described in Example 25, the following compounds were prepared starting from 6-methoxy-1,2,3,4-tetrahydroquinoline and the appropriate chloroacyl chloride:

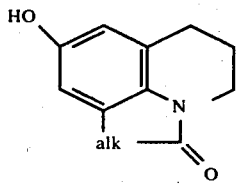

| Example | alk | m.p. °C | Analysis (theoretical in brackets) | | |
|---|---|---|---|---|---|
| | | | C % | H % | N % |
| 25 | —CH—<br>\|<br>CH₃ | 197–200° | 70.23<br>(70.91 | 6.50<br>6.45 | 6.82<br>6.89) |
| 27 | —CH₂CH₂— | 230–5° | 70.52<br>(70.91 | 6.56<br>6.45 | 6.53<br>6.89) |

EXAMPLE 28

9-Hydroxy-2,3,6,7-tetrahydro-1H,5H-pyrido-[3,2,1-i,j]-quinolin-3-one (the compound of Example 27) (0.5 g) was added to benzene (20 ml) containing sodium acetate (0.1 g) and acetic anhydride (0.3 ml), and the mixture was refluxed for 3 hours. After cooling, the sodium acetate was removed by filtration and the solution was evaporated in vacuo to dryness. The resultant solid was washed with 60°–80° petroleum ether and crystallised from a mixture of benzene and 60°–80° petroleum ether to yield 0.33 g of 9-acetoxy-2,3,6,7-tetrahydro-1H,5H-pyrido-[3,2,1-i,j]-quinolin-3-one as pale yellow crystals, m.p. 124°–6°.

Analysis:
Found: C, 68.56; H, 6.17; N, 5.68%. Calculated for $C_{14}H_{15}NO_3$: C, 68.10; H, 6.24; N, 5.28%.

EXAMPLES 29 and 30

By procedures similar to that described in Example 28, the following two compounds were prepared starting from the compounds of Examples 25 and 26, respectively.

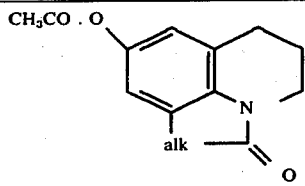

| Example | alk | m.p. °C | Analysis (theoretical in brackets) | | |
|---|---|---|---|---|---|
| | | | C % | H % | N % |
| 29 | —CH₂— | 140–2° | 67.71<br>(67.52 | 5.71<br>5.67 | 6.33<br>6.06) |
| 30 | —CH—<br>\|<br>CH₃ | 130–1° | 68.55<br>(68.10 | 6.16<br>6.24 | 5.71<br>5.28) |

EXAMPLE 31

A solution of 8-bromo-1,2,5,6-tetrahydro-4-H-pyrrolo-[3,2,1-i,j]-quinolin-4-one (prepared as in Example 7) (1.5 g) and cuprous cyanide (0.63 g) in N-methyl-2-pyrrolidone (13 ml) was refluxed for 6 hours, and then allowed to cool to room temperature, whereupon a precipitate had formed. The precipitate (700 mg) was collected by filtration and 400 mg thereof recrystallised from ethanol, yielding 250 mg of 8-cyano-1,2,5,6-tetrahydro-4H-pyrrolo-[3,2,1-i,j]-quinolin-4-one, m.p. 204°–5°.

Analysis:
Found: C, 72.96; H, 5.02; N, 14.20%.
Calculated for $C_{12}H_{10}N_2O$: C, 72.71; H, 5.09; N, 14.13%.

EXAMPLE 32

A. A solution of 6-methyl-1,2,3,4-tetrahydroquinoline (3.0 g) and ethyl acetoacetate (2.8 g) in xylene (7.0 ml) containing 2 drops of dry pyridine was refluxed for 12 hours. The solution was then allowed to cool to room temperature, washed in turn with 2N hydrochloric acid (2× 20 ml) and water (2 × 20 ml), dried over anhydrous magnesium sulphate and evaporated under reduced pressure at 100° to dryness, yielding 1-acetoacetyl-6-methyl-1,2,3,4-tetrahydroquinoline (1.7 g) as a crude solid, to be used directly in the next stage.

B. The product of (A) (1.6 g) was slowly added to concentrated sulphuric acid (2 ml) with stirring, keeping the temperature below 100°. The mixture was then heated on a steam bath for 15 minutes and poured onto ice, the aqueous solution then being basified by addition of dilute sodium hydroxide solution and extracted with chloroform. Evaporation of the previously dried chloroform solution in vacuo yielded a solid, which was crystallised from a mixture of benzene and 60°–80° petroleum ether to afford crystals (0.7 g) of 1,9-dimethyl-6,7-dihydro-5H-pyrido-[3,2,1-i,j]-quinoline-3-one, m.p. 136°–7°.

Analysis:
Found: C, 79.34; H, 6.90; N, 6.61%. Calculated for $C_{14}H_{15}NO$: C, 78.84; H, 7.09; N, 6.57%.

EXAMPLE 33

By a procedure similar to that described in Example 32, 1-methyl-9-methoxy-6,7-dihydro-5H-pyrido-[3,2,1-i,j]-quinolin-3-one, m.p. 115°–7°, was prepared starting from 6-methoxy-1,2,3,4-tetrahydroquinoline and ethyl acetoacetate.

Analysis:
Found: C, 73.34; H, 6.60; N, 6.03%. Calculated for $C_{14}H_{15}NO_2$: C, 72.76; H, 6.59; N, 6.11%.

EXAMPLE 34

A. A mixture of indoline (9.5 g) and ethyl α-ethylacetoacetate was refluxed for 1 hour and then submitted to a distillation to remove ethanol formed in the reaction, 2 ml thereof being collected. The residual oil was then poured into water and the mixture acidified by addition of dilute hydrochloric acid and extracted with chloroform, the organic solution then being dried over anhydrous magnesium sulphate and evaporated in vacuo to afford an oil (22.5 g) which solidified on standing. The crude product, 1-(α-ethylacetoacetyl)-indoline was then crystallised from cyclohexane prior to use in the next stage.

B. The product of (A) (2.0 g) and polyphosphoric acid (2.0 g) were heated together at 150° for 1 hour and then poured into water. The mixture was extracted with chloroform, the organic solution then being washed with water, dried over anhydrous magnesium sulphate and evaporated in vacuo to afford an oil, which subsequently solidified on standing. Crystallisation of the crude product from cyclohexane yielded 5-ethyl-6-methyl-1,2-dihydro-4H-pyrrolo-[3,2,1-i,j]-quinolin-4-one, m.p. 83°–4°.
Analysis:
Found: C, 78.78; H, 7.13; N, 6.10%. Calculated for $C_{14}H_{15}NO$: C78.84; H, 7.09; N, 6.75%.

EXAMPLE 35

By a procedure similar to that described in Example 34, 6-phenyl-1,2-dihydro-4H-pyrrolo-[3,2,1-i,j]-quinolin-4-one, m.p. 177.5°–178.5°. was prepared starting from indoline and ethyl benzoylacetate.
Analysis: Found: C, 82.43; H, 5.29; N, 5.66%. Calculated for $C_{17}H_{13}No$: C, 82.56; H, 5.30; N, 5.66%.

EXAMPLE 36

A mixture of indoline (5.95 g) and α-methyl diethyl malonate (8.7 g) was refluxed under an air condenser for 2 hours, after which time all the ethanol formed in the reaction had evolved and excess α-methyl diethyl malonate was distilling off. The mixture was allowed to cool to room temperature, the whole mass solidifying by this stage, and the solid was crystallised from acetic acid to yield 6.3 g of 6-hydroxy-5-methyl-1,2-dihydro-4H-pyrrolo-[3,2,1-i,j]-quinolin-4-one, m.p. 300°, with decomposition.
Analysis:
Found: C, 71.25; H, 5.56; N, 6.62%. Calculated for $C_{12}H_{11}NO_2$: C, 71.62; H, 5.57; N, 6.96%.
This compound is the enolic form of 5-methyl-1,2,5,6-tetrahydro-4H-pyrrolo-[3,2,1-i,j]-quinolin-4,6-dione.

EXAMPLE 37

By a procedure similar to that described in Example 36, 1-hydroxy-2-methyl-6,7-dihydro-5H-pyrido-[3,2,1-i,j]-quinolin-3-one, m.p. 200°–2°, was prepared from tetrahydroquinoline and α-methyl diethyl malonate.
Analysis:
Found: C, 72.59; H, 5.96; N, 6.62%. Calculated for $C_{13}H_{13}NO_2$: C, 72.54; H, 6.04; N, 6.51%.
This compound is the enolic form of 2-methyl-2.3.6.7-tetrahydro-1H,5H-pyrido-[3,2,1-i,j]-quinolin-1,3-dione.

EXAMPLE 38

1-Hydroxy-2-methyl-6,7-dihydro-5H-pyrido-[3,2,1-i,j]-quinolin-3-one (prepared as in Example 37) (2.8 g) and phosphorus pentachloride (2.5 g) were intimately mixed by grinding together with a pestle and mortar. To the powder was added a small amount of phosphoryl chloride, and the mixture was then gently heated to 120° and maintained at that temperature for ½ hour, after which the resultant melt was allowed to cool to room temperature and dissolved in concentrated hydrochloric acid. The solution was diluted by addition to water (50 ml) and basified with sodium hydroxide solution; whereupon a brown precipitate formed. Collection of the precipitate by filtration and two recrystallisations from cyclohexane yielded 300 mg of 1-chloro-2-methyl-6,7-dihydro-5H-pyrido-[3,2,1-i,j]-quinolin-3-one, m.p. 138°–140°.
Analysis:
Found: C, 66.90; H, 5.24; N, 6.21%. Calculated for $C_{13}H_{12}ClNO$: C, 66.45; H, 5.11; N, 5.96%.

EXAMPLE 39

Phosphorus pentasulphide (1.1 g) was added in small portions over a 15 minute period to a solution of 1,2,5,6-tetrahydro-4H-pyrrolo-[3,2,1-i,j]-quinolin-4-one (1.73 g) in dry pyridine (12.5 ml) with shaking. The solution was then refluxed for 10 minutes, cooled, and poured into water, the resultant precipitate then being collected by filtration and dried. Produced was 1.3 g of crude product, m.p. 115°–7°.
Soxhlet extraction with 60°–80° petroleum ether afforded, after evaporation of the solution to dryness, 1.0 g of pale yellow crystals. Recrystallisation of the latter from n-hexane afforded 0.6 g of 1,2,5,6-tetrahydro-4H-pyrrolo-[3,2,1-i,j]-quinolin-4-thione, m.p. 126°–126.5°.
Analysis:
Found: C, 69.60; H, 5.89; N, 7.30%. Calculated for $C_{11}H_{11}NS$: C, 69.80; H, 5.86; N, 7.41%.

EXAMPLES 40 TO 42

By procedures similar to that described in Example 39, the following thiones were prepared starting from the corresponding oxo compounds and phosphorus pentasulphide. The oxo compound starting materials were the known compounds 2-lilolidone, 6-methyl-1,2-dihydro-4H-pyrrolo-[3,2,1-i,j]-quinolin-4-one, and 3julolidone respectively, the second of these being prepared by the method of Example 34 from indoline and ethyl acetoacetate.
The known compound 1,2-dihydro-4H-pyrrolo-[3,2,1-i,j]quinolin-4-thione was similarly prepared from the corresponding 4-ketone.

| Example | Structure | m.p. °C | Analysis (theoretical in brackets) | | |
|---|---|---|---|---|---|
| | | | C % | H % | N % |
| 40 | 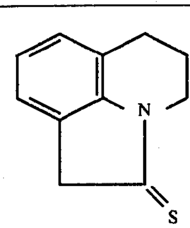 | 121–3° | 69.31 (69.80 | 5.83 5.85 | 7.02 7.41) |

-continued

| Example | Structure | m.p. °C | Analysis (theoretical in brackets) C % | H % | N % |
|---|---|---|---|---|---|
| 41 | (structure with CH₃) | 235–236.5° | 71.16 (71.60 | 5.37 5.52 | 7.47 6.97) |
| 42 | (structure) | 73–5° | 71.06 (70.93 | 6.57 6.40 | 6.97 6.90) |

EXAMPLE 43

By a similar procedure to that described in Examples 7 and 8, 9-bromo-2,3,6,7-tetrahydro-1H, 5H-pyrido-[3,2,1-i,j]-quinolin-3-one, m.p. 101°–102°, was prepared from 3-julolidone.
Analysis:
Found: C, 54.21; H, 4.45; N, 5.41%. Calculated for $C_{12}H_{12}BrNO$: C, 54.0; H, 4.51; N, 5.21%.

EXAMPLE 44

Phosphorus oxychloride (52g) was mixed with N-methyl formanilide (8.6g) at room temperature and then a solution of 2-lilolidone (17.2g) in ether (600 ml) was added. A homogeneous solution was formed on shaking and allowed to stand overnight, when an oily layer separated. The mixture was poured onto ice, washed with dilute acid and then with water, extracted with chloroform and the organic layer separated, dried and evaporated to yield 3.5g of crude 8-formyl-1,2,5,6-tetrahydro-4H-pyrrolo-[3,2,1-i,j]-quinolin-2-one as a yellow solid. Recrystallisation from acetic acid yielded 2.2g of product, m.p. 210°–213°.
Analysis:
Found: C, 71.63; H, 5.73; N, 7.27%. Calculated for $C_{12}H_{11}NO_2$ C, 71.7; H, 5.5; N, 6.96%.

EXAMPLES 45 AND 46

The following compounds were prepared by the method of Example 34, from 1,2,3,4-tetrahydroquinoline and ethyl α-n-propylacetoacetate, and from 6-methoxy-1,2,3,4-tetrahydroquinoline and ethyl α-methyl-acetoacetate, respectively:
1-methyl-2-propyl-6,7-dihydro-3H,5H-pyrido-[3,2,1-i,j]-quinolin-3-one, m.p. 121°–123°.
Analysis:
Found: C, 78.97; H, 7.40; N, 6.34%. Calculated for $C_{16}H_{19}NO$: C, 79.26; H, 7.54; N, 6.16%.

9-methoxy-1,2-dimethyl-6,7-dihydro-3H,5H-pyrido-[3,2,1-i,j]-quinolin-3-one, m.p, 115°–117°.
Analysis:
Found: C, 73.77; H, 7.08; N, 5.8%. Calculated for $C_{14}H_{19}NO_2$:C, 74.05; H, 7.04; N, 5.7%.

EXAMPLE 47 AND 48

By a similar procedure to that described in Example 36, the following compounds were prepared from indoline and α-phenyl diethyl malonate and α-n-butyl diethyl malonate, respectively.
a.  6-hydroxy-5-phenyl-1,2-dihydro-4H-pyrrolo-[3,2,1-i,j]-quinolin-4-one, m.p. 301°–303°.
Analysis:
Found: C, 77.49; H, 4.78; N, 5.45%. Calculated for $C_{17}H_{13}NO_2$ C, 77.55; H, 4.98; N, 5.32%.
This compound is the enolic form of 5-phenyl-1,2,5,6-tetrahydro-4H-pyrrolo-[3,2,1-i,j]-quinolin-4,6-dione.
b.  5-n-butyl-6-hydroxy-1,2-dihydro-4H-pyrrolo-[3,2,1-i,j]-quinolin-4-one, m.p. 164°–166°.
Analysis:
Found: C, 73.79; H, 7.14; N, 5.60%. Calculated for $C_{15}H_{17}NO_2$: C, 74.05; H, 7.04; N, 5.76%.

Examples 49 TO 60

By a similar procedure to that described in Example 36, the compounds shown in the following Table were prepared from the appropriately substituted tetrahydroquinoline and α-substituted diethyl malonate:

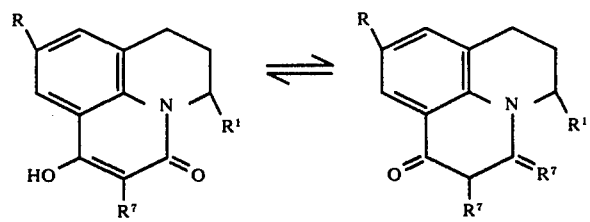

| Example | R | R¹ | R⁷ | m.p. °C | Analysis (calculated in brackets) C | H | N |
|---|---|---|---|---|---|---|---|
| 49 | CH₃O | H | CH₃ | 234–237° | 68.57 | 6.16 | 6.01 |

-continued

| Example | R | $R^1$ | $R^7$ | m.p. °C | Analysis (calculated in brackets) C | H | N |
|---|---|---|---|---|---|---|---|
| 50 | H | H | $C_6H_5$ | 227–230° | 78.25 (77.96 | 6.16 5.61 5.45 | 5.71) 5.48 5.05) |
| 51 | $CH_3O$ | H | H | 295–300° | 67.40 (67.52 | 5.62 5.67 | 6.02 6.06) |
| 52 | H | H | $C_2H_5$ | 195–197° | 73.16 (73.34 | 6.60 6.59 | 6.12 6.11) |
| 53 | H | H | $n-C_3H_8$ | 164–166° | 74.13 (74.05 | 7.05 7.04 | 5.98 5.76) |
| 54 | H | $CH_3$ | $CH_3$ | 197–200° | 73.04 (73.34 | 6.70 6.59 | 5.87 6.11) |
| 55 | $CH_3O$ | H | $C_6H_5$ | 214–215° | 74.29 (74.25 | 5.61 5.58 | 4.56 4.56) |
| 56 | $CH_3$ | H | $C_2H_5$ | 286–288° | 74.12 (74.05 | 7.09 7.04 | 6.01 5.76) |
| 57 | $CH_3$ | H | $iso-C_3H_8$ | 269–271° | 74.95 (74.68 | 7.58 7.44 | 5.16 5.44) |
| 58 | $CH_3$ | H | $iso-C_3H_8$ | 198–200° | 74.13 (74.05 | 7.03 7.04 | 5.47 5.76) |
| 59 | $CH_3O$ | H | $iso-C_3H_8$ | 178–180° | 71.25 (74.05 | 7.31 7.30 | 4.53 4.87) |
| 60 | H | H | $n-C_4H_9$ | 166–168° | 74.75 (74.68 | 7.52 7.44 | 5.10 5.44) |

Examples 61 TO 64

By a similar procedure to that described in Example 38, the compounds shown in the following Table were prepared from the products of Examples 36, 50, 37, and 49, respectively:

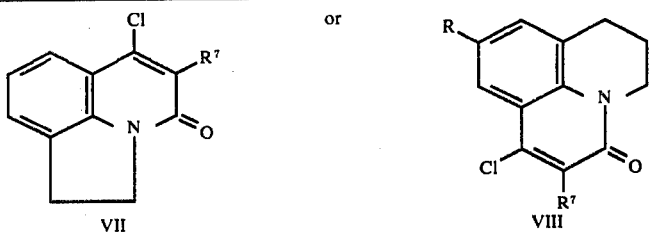

| Example | Formula | R | $R^7$ | m.p. ° C | Analysis (calculated in brackets) C | H | N |
|---|---|---|---|---|---|---|---|
| 61 | VII | H | $CH_3$ | 168–170° | 63.92 (63.90 | 4.77 4.73 | 6.03 6.22) |
| 62 | VIII | $CH_3O$ | H | 138–9° | 62.70 (62.51 | 4.85 4.95 | 5.30 5.62) |
| 63 | VIII | H | $CH_3$ | 121–2° | 62.74 (62.76 | 5.18 5.41 | 5.21 5.21) |
| 64 | VIII | H | $C_6H_5$ | 114–6° | 73.20 (73.10 | 4.77 4.74 | 4.67 4.74) |

EXAMPLE 65

The product of Example 61 (3.3g) in ethanol (70 ml) was hydrogenated using a 5% palladium-on-carbon catalyst in a Parr hydrogenator at 60° and 60 psi until the required amount of hydrogen had been taken up. The reaction product was filtered to remove catalyst and the ethanol evaporated off to yield an off-white solid which was recrystallised from 60/80 petroleum ether to give 1-methyl-1,2,5,6-tetrahydro-4H -pyrrolo-[3,2,1-i,j]-quinolin-4-one, m.p. 81–82°.

Analysis:
Found: C, 76.84; H, 7.12; N, 7.45. Calculated for $C_{12}H_{13}NO$: C, 76.97; H, 7.00; N, 7.48.

The use of compounds of the formula I, including novel compounds of the invention, to protect rice plants against the blast disease caused by *Piricularia oryzae* is illustrated by the following Example.

EXAMPLE 66

Rice plants in the fully developed second-leaf growth stage were subjected to a spray of the test compound until run-off. Each test compound was dissolved in water, acetone, methanol or ethanol and dilute to 100 parts per million with deionised water containing a wetting agent (Span 85) and a dispersing agent (Tween 80) used at levels of 200 ppm. and 50 ppm., respectively, in the final spray. ("Span" and "Tween" are Registered Trade Marks.)

The treated plants were allowed to dry, spray-inoculated with an aqueous spore suspension of *Piricularia oryzae* (200 spores/microscopic field at 100 X) to run-off and then placed in an incubation chamber at 70° F and 95 percent relative humidity. After about thirty hours incubation, the plants were removed to a greenhouse for disease development. Untreated plants were inoculated and treated similarly, as controls. Within five days infection lesions were sufficiently developed to permit assessment of the effectiveness of the test compounds in controlling the disease.

The severity of the infection was determined by actual count of the number of infection lesions appearing on the treated plants compared to the number of lesions appearing on the control plants. Phenyl mercuric acetate (PMAS) was used as a reference standard. Rice plants were treated with an aqueous spray of this standard material as described above, at a concentration of 200 ppm.; at which level it was found to be 100% effective.

In this manner, the effectiveness of the following compounds against rice blast disease was demonstrated (at 100 parts per million unless otherwise indicated). An asterick in the "Example" column indicates a known compound.

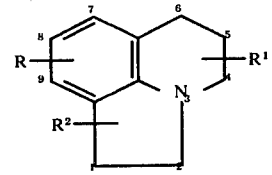

| R | R$^1$ | R$^2$ | Example | Effectiveness (%) |
|---|---|---|---|---|
| H | H | H | * (lilolidine[1]) | 56 |
| H | H | 2-oxo | * (2-lilolidone) | 100 |
| H | 4-oxo | H | * (4-lilolidone) | 100 |
| H | 6-oxo | H | * (6-lilolidone) | 55 |
| H | H | 1-CH$_3$-2-oxo | * | 96 |
| H | H | 1-C$_6$H$_5$-2-oxo | * | 37 (at 50 ppm) |
| 8-CH$_3$ | H | 2-oxo | 1 | 99 |
| 8-CH$_3$ | H | 1-C$_6$H$_5$-2-oxo | 3 | 49 |
| H | 4-CH$_3$ | 2-oxo | 4 | 55 |
| 8-Cl | H | 1,1-di-Cl-2-oxo | 5 | 68 |
| 7,8-di-Cl | H | 1,1-di-Cl-2-oxo | 6 | 60 |
| 8-Br | 4-oxo | H | 7 | 98 |
| 8-Br | H | 2-oxo | 8 | 87 |
| 8-Br | H | 1-Br-1-C$_6$H$_5$-2-oxo | 9 | 53 |
| 8-Br | H | 1-Br-1-CH$_3$-2-oxo | 10 | 33 |
| 8-Br | H | 1,1-di-Cl-2-oxo | 11 | 70 |
| 8-C$_2$H$_5$CO | 4-oxo | H | 12 | 74 |
| 8-C$_2$H$_5$CO | H | 1-CH$_3$-2-oxo | 13 | 51 |
| 8-n-C$_3$H$_8$CO | H | 1-CH$_3$-2-oxo | 14 | 17 |
| 8-CH$_3$CO | H | 2-oxo | 15 | 53 |
| 8-C$_2$H$_5$CO | H | 2-oxo | 16 | 43 |
| 8-CH$_3$CO | 4-oxo | H | 17 | 92 |
| 8-C$_6$H$_5$CO | H | 2-oxo | 19 | 94 |
| 8-Cl | H | 1,2-dioxo | 20 | 38 |
| 8-Br | H | 1,2-dioxo | 21 | 50 |
| 8-Cl | H | 2-oxo | 22 | 72 |
| 8-Cl | H | 1,1-di-C$_6$H$_5$-2-oxo | 23 | 30 |
| 8-tert-C$_4$H$_9$ | H | 2-oxo | 24 | 99 |
| 8-HO | H | 2-oxo | 25 | 54 |
| 8-HO | H | 1-CH$_3$-2-oxo | 26 | 30 |
| 8-CH$_3$CO.O | H | 1-CH$_3$-2-oxo | 30 | 48 |
| 8-CN | H | 4-oxo | 31 | 37 |
| H | 5-CH$_3$-4,6-dioxo | H | 36 | 53 (at 10 ppm) |
| H | H | 4-thio | 39 | 100 |
| H | H | 2-thio | 41 | 57 |
| 8-HCO | H | 2-oxo | 44 | 58 |
| H | 5CH$_3$-4-oxo | H | 65 | 34 |
| H | 4-oxo | H | * | 99 |
| H | 6-CH$_3$-4-oxo | H | * | 100 |
| H | 4-thio | H | * | 75 |
| H | 5,6-di-CH$_3$-4-oxo | H | * | 40 (at 50 ppm) |
| H | 5-C$_2$H$_5$-6-CH$_3$-4-oxo | H | 34 | 43 (at 10 ppm) |
| H | 6-C$_6$H$_5$-4-oxo | H | 35 | 49 |
| H | 6-CH$_3$-4-thio | H | 40 | 53 (at 10 ppm) |
| H | 6-Cl-5-CH$_3$-4-oxo | H | 61 | 53 (at 10 ppm) |

[1]as p-toluene sulphonate salt

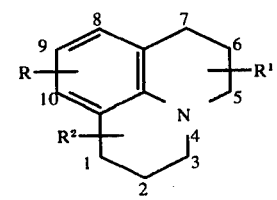

| R | R$^1$ | R$^2$ | Example | Effectiveness (%) |
|---|---|---|---|---|
| H | H | 3-oxo | *(3-julolidone) | 99 |
| H | H | 1,3-dioxo | * | 58 |
| 9-CH$_3$ | H | 3-oxo | 2 | 79 |
| 9-CH$_3$CO.O | H | 3-oxo | 28 | 56 |
| H | H | 3-thio | 42 | 100 |
| H | H | 2-C$_6$H$_5$-1,3-dioxo | 50 | 64 (at 10 ppm) |
| H | H | 2-n-C$_3$H$_8$-1,3-dioxo | 53 | 61 |
| H | H | 2-CH$_3$-1,3-dioxo | 54 | 63 |

| | | -continued | | |
|---|---|---|---|---|
| 9-CH$_3$O | H | 2-C$_6$H$_5$-1,3-dioxo | 55 | 29 |
| 9-CH$_3$ | H | 2-iso-C$_3$H$_8$-1,3-dioxo | 57 | 47 |
| H | H | 2-iso-C$_3$H$_8$-1,3-dioxo | 58 | 65 (at 10 ppm) |
| H | H | 3-oxo | * | 96 |
| H | H | 1-CH$_3$-3-oxo | * | 56 |
| H | H | 1-Cl-3-oxo | * | 64 (at 10 ppm) |
| 9-CH$_3$ | H | 1-CH$_3$-3-oxo | 32 | 31 |
| 9-CH$_3$O | H | 1-CH$_3$-3-oxo | 33 | 30 |
| H | H | 1-Cl-2-CH$_3$-3-oxo | 38 | 52 (at 10 ppm) |
| 9-CH$_3$O | H | 1-Cl-3-oxo | 62 | 38 |
| H | H | 1-Cl-2-CH$_3$-3-oxo | 63 | 47 |
| H | H | 1-Cl-2-C$_6$H$_5$-3-oxo | 64 | 39 |

What we claim is:

1. A method for the control of fungal diseases of rice plants and disease thereof caused by Xanthomonas oryzae comprising contacting the plants, or the seeds thereof, with a fungicidally or bactericidally effective amount in a compatible diluent of a compound of the formula

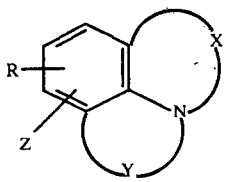

or a non-phytotoxic acid addition salt thereof;

wherein each of X and Y completes a saturated or unsaturated pyrido ring;

X and Y are each unsubstituted or substituted with up to two substituents which are halo, lower alkyl, phenyl, oxo or thio;

R is hydrogen, lower alkyl, lower alkoxy, lower alkanoyl, benzoyl, hydroxy, lower alkanoyloxy, cyano, or halo; and Z is hydrogen or halo.

2. A method according to claim 1, in which said compound is 3-julolidone, julolidine-3-thione or 1,2-dihydro-3H,5H-pyrido-[3,2,1-i,j]-quinolin-5-one.

3. A method according to claim 1 in which said compound is added to the water in which said rice plant is growing.

* * * * *

UNITED STATES PATENT AND TRADEMARK OFFICE
CERTIFICATE OF CORRECTION

PATENT NO. : 4,008,325
DATED : FEBRUARY 15, 1977
INVENTOR(S) : Robert J. Bass et al It is certified that error appears in the above-identified patent and that said Letters Patent are hereby corrected as shown below:

Column 27/line 49 first table delete "$^1$as p-toluene sulphonate salt".

Columns 27 and 28 first table line 34 under columns "$R^1$" and "$R^2$" change "H" and "4-oxo" to -- 4-oxo -- and --H--.

Columns 27 and 28 first table line 36 under columns "$R^1$" and "$R^2$" change "H" and "4-thio" to -- 4-thio -- and --H--.

Columns 27 and 28 first table after line 39 in the body of the table (i.e. after the line which reads "H   5CH$_3$-4-oxo   H   65   34") insert -- (1) as p-toluene sulphonate salt

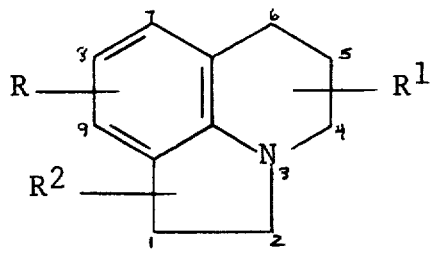

| R | $R^1$ | $R^2$ | Example | Effectiveness % |
---.

Page 2 of 2

UNITED STATES PATENT AND TRADEMARK OFFICE
CERTIFICATE OF CORRECTION

PATENT NO. : 4,008,325
DATED : February 15, 1977
INVENTOR(S) : Robert J. Bass et al It is certified that error appears in the above-identified patent and that said Letters Patent are hereby corrected as shown below:

```
              first table
Columns 29 and 30/after line 3 in the body of the table (i.e.
  after the line which reads "H      H      2-iso-C3H8-1,3-dioxo
  58      65 (at 10 ppm)") insert
```

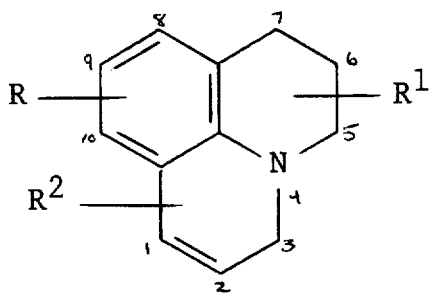

R    R¹    R²    Example    Effectiveness %

Signed and Sealed this

Twenty-fifth Day of October 1977

[SEAL]

Attest:

RUTH C. MASON
Attesting Officer

LUTRELLE F. PARKER
Acting Commissioner of Patents and Trademarks